(12) United States Patent
Basinski et al.

(10) Patent No.: US 6,395,509 B1
(45) Date of Patent: May 28, 2002

(54) DNA ENCODING RHESUS OB PROTEIN

(75) Inventors: Margret B. Basinski, Indianapolis; Brigitte E. Schoner, Monrovia, both of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 08/452,228

(22) Filed: May 26, 1995

(51) Int. Cl.⁷ .......................... C12P 21/06; C07H 17/00

(52) U.S. Cl. ................ 435/69.1; 435/320.1; 435/252.3; 435/325; 435/71.1; 536/23.5; 536/23.51

(58) Field of Search .......................... 530/350; 536/23.5, 536/23.51; 435/69.1, 320.1, 240.1, 71.1, 252.3, 325

(56) References Cited

U.S. PATENT DOCUMENTS 4,626,549 A    12/1986   Molloy et al. ............... 514/651

FOREIGN PATENT DOCUMENTS

WO    WO96/05309    2/1996

OTHER PUBLICATIONS

Martial et al. 1979 Science 205:602–607.*
U.S. application No. 08/381,048 DiMarchi et al., filed Jan. 31, 1995.
U.S. application No. 08/383,638, Basinski et al., filed Feb. 6, 1995.
U.S. application No. 08/381,033, DiMarchi et al., filed Jan. 31 1995.
U.S. application No. 08/383,631, Basinski et al., filed Feb. 6, 1995.
U.S. application No. 08/381,265, DiMarchi et al., filed Jan. 31, 1995.
U.S. application No. 08/383,648, Basinski et al., filed Feb. 6, 1995.
U.S. application No. 08/381,247, DiMarchi et al., filed Jan. 31, 1995.
U.S. application No. 08/383,632, Basinski et al., filed Feb. 6, 1995.
U.S. application No. 08/381,266, DiMarchi et al., filed Jan. 31, 1995.
U.S. application No. 08/384,492, DiMarchi et al., filed Feb. 6, 1995.
U.S. application No. 08/381,047, DiMarchi et al., filed Jan. 31, 1995.
U.S. application No. 08/383,649, Basinski et al., filed Feb. 6, 1995.
U.S. application No. 08/381,057, DiMarchi et al., filed Jan. 31, 1995.
U.S. application No. 08/381,050, DiMarchi et al., filed Jan. 31, 1995.
U.S. application No. 08/381,034, DiMarchi et al., filed Jan. 31, 1995.
U.S. application No. 08/381,040, DiMarchi et al., filed Jan. 31, 1995.
U.S. application No. 08/381,163, DiMarchi et al., filed Jan. 31, 1995.
U.S. application No. 08/381,054, DiMarchi et al., filed Jan. 31, 1995.
U.S. application No. 08/381,041, DiMarchi et al., filed Jan. 31, 1995.
U.S. application No. 08/381,370, DiMarchi et al., filed Jan. 31, 1995.
U.S. application No. 08/381,451, DiMarchi et al., filed Jan. 31, 1995.
U.S. application No. 08/383,658, Fukuchi, filed Feb. 6, 1995.
U.S. application No. 08/381,031, DiMarchi et al., filed Jan. 31, 1995.
U.S. application No. 08/383,639, Basinski et al., filed Feb. 6, 1995.
U.S. application No. 08/381,458, DiMarchi et al., filed Jan. 31, 1995.
U.S. application No. 08/384,183, Basinski et al., filed Feb. 6, 1995.
U.S. application No. 08/381,661, DiMarchi et al., filed Jan. 31, 1995.
U.S. application No. 08/384,292, Basinski et al., filed Feb. 6, 1995.
U.S. application No. 08/381,666, DiMarchi et al., filed Jan. 31, 1995.
U.S. application No. 08/406,354, DiMarchi et al., filed Mar. 17, 1995.
U.S. application No. 08/398,021, Becker et al., filed Mar. 3, 1995.
U.S. application No. 08/381,049, DiMarchi et al., filed Jan. 31, 1995.
U.S. application No. 08/381,037, DiMarchi et al., filed Jan. 31, 1995.
U.S. application No. 08/384,493, Basinski et al., filed Feb. 6, 1995.
U.S. application No. 08/381,264, Heath et al., filed Jan. 31, 1995.
Chem. Abstract 94–304407/38, Nagata Sangyo Co. Ltd. (Mar. 29, 1993).
Zhang, et al., "Positional cloning of the mouse obese gene and its human homologue", *Nature*, 372:1, 425–432 (Dec. 1, 1994).
Rink, "In search of a satiety factor", *Nature*, 372:1, 406–407 (Dec. 1, 1994).
Flam, "Obesity Gene Discovery May Help Solve Weighty Problem", *Science*, 266, 1477–1478 (Dec. 2, 1994).
Murakami, et al, "Cloning of Rat Obese cDNA And Its Expression In Obese Rats⁺", *Biochemical and Biophysical Research Communications*, 209:3, 944–952.

\* cited by examiner

*Primary Examiner*—Karen Cochrane Carlson
(74) *Attorney, Agent, or Firm*—Mark J. Stewart

(57) ABSTRACT

The invention includes isolated nucleic acid molecules encoding a Rhesus ob gene product that regulates obesity in mammals. A preferred embodiment consisting of a native DNA sequence is disclosed, as are vectors and methods for expressing the Rhesus ob gene product.

8 Claims, No Drawings

DNA ENCODING RHESUS OB PROTEIN

The invention belongs to the general field of molecular biology as applied to biopharmaceutical research and development. The invention includes nucleic acid compounds, vectors and methods useful for expressing proteins that help regulate the body's volume of adipose tissue.

BACKGROUND OF THE INVENTION

Obesity, especially upper body obesity, is a common and very serious public health problem in the United States and throughout the world. According to recent statistics, more than 25% of the U.S. population and 27% of the Canadian population are over weight. Kuczmarski, *Amer. J. of Clin. Nut.* 55: 495S–502S (1992); Reeder et al., *Can. Med. Ass. J,* 23: 226–233 (1992). Upper body obesity carries the highest risk factor known for Type II Diabetes and is a significant risk factor for cardiovascular disease and cancer as well. Recent cost estimates for medical complications associated with obesity are $150 billion world wide. The problem has now become so serious that the Surgeon General has begun a national initiative to combat obesity in America.

Hypertension, dyslipidemia, and insulin resistance are the primary pathologies associated with obesity. Many studies have demonstrated that weight reduction through diet and exercise dramatically improves these serious medical conditions. Unfortunately, obese individuals generally fail to significantly reduce their body mass through diet and exercise and have a near 95% failure rate. This failure may be due to genetically inherited factors that contribute to increased appetite, preference for high calorie foods, reduced physical activity, reduced lipolytic metabolism, and increased lipogenic metabolism. This indicates that people inheriting these genetic traits are prone to becoming obese regardless of their efforts to combat the condition. Therefore, new pharmacological agents that can reverse obesity in spite of genetic predisposition are needed.

The ob/ob mouse model of obesity and diabetes is known to carry an autosomal recessive trait linked to a mutation in the sixth chromosome. Recently, Zhang and co-workers published the positional cloning of a mouse gene linked to this condition. Zhang et al. *Nature* 372: 425–32 (1994). This report discloses a mouse cDNA sequence encoding a 167 amino acid protein that is expressed exclusively in adipose tissue and compares this mouse ob gene product to a human homolog. The report also discloses a point mutation resulting in the conversion of an Arg codon to a stop codon at position 105. This mutant gene is postulated to expresses a truncated protein that lacks the biological function of the complete intact protein.

Physiologist have long postulated that excess fat cells laid down through overeating signals the brain that the body is obese which, in turn, causes the body to eat less and burn more fuel. G. R. Hervey, *Nature* 227: 629–631 (1969). Parabiotic experiments support a "feedback" model and suggest that a circulating peptide hormone may regulate the size of the body's fat depot. The newly disclosed ob gene product mentioned above is now believed to be such a hormone.

The present invention is based on the discovery of a an obesity gene cloned from Rhesus monkey adipose tissue. Therefore, this invention is useful for producing what is currently believed to be a biologically active anti-obesity protein useful for treating obesity and reducing the risk for Type II diabetes, cardiovascular diseases, and cancer in mammals.

The invention is also useful in a Rhesus immunogenicity model. In this mode, the invention can be used to predict the immunogenic capacity of analogs of the human ob gene product. For example, if one wished to determine whether a specific substitution in the human ob gene product would produce an antibody response in humans, the corresponding substitution could be made in the Rhesus ob protein. The Rhesus analog is then injected into a Rhesus monkey and its immunological response monitored. If the subtitution failed to produce an immunological response, one would then accurately predict that the corresponding substitution in the human ob protein also would not raise an immunological response in a human.

SUMMARY OF THE INVENTION

The invention is drawn to isolated nucleic acid molecules consisting of a nucleotide sequence that encodes a protein having the amino acid sequence of SEQ ID NO: 2. Recombinant DNA vectors and host cells comprising such nucleic molecules make up further embodiments of the invention. Processes for producing anti-obesity proteins comprising culturing such host cells and isolating a protein comprising the amino acid sequence of SEQ ID NO: 2 is also claimed.

DETAILED DESCRIPTION OF THE INVENTION

For purposes of the present invention, as disclosed and claimed herein, the following terms and abbreviations are defined as follows:

Base pair (bp)—refers to DNA or RNA. The abbreviations A,C,G, and T correspond to the 5'-monophosphate forms of the nucleotides (deoxy)adenine, (deoxy)cytidine, (deoxy)guanine, and (deoxy)thymine, respectively, when they occur in DNA molecules. The abbreviations U,C,G, and T correspond to the 5'-monophosphate forms of the nucleosides uracil, cytidine, guanine, and thymine, respectively when they occur in RNA molecules. In double stranded DNA, base pair may refer to a partnership of A with T or C with G. In a DNA/RNA heteroduplex, base pair may refer to a partnership of T with U or C with G.

DNA—Deoyxribonucleic acid.

RNA—Ribonucleic acid Nucleic acid molecule—DNA or RNA.

Plasmid—an extrachromosomal self-replicating genetic element.

Reading frame—the nucleotide sequence from which translation occurs "read" in triplets by the translational apparatus of tRNA, ribosomes and associated factors, each triplet corresponding to a particular amino acid. Because each triplet is distinct and of the same length, the coding sequence must be a multiple of three. A base pair insertion or deletion (termed a frameshift mutation) may result in two different proteins being coded for by the same DNA segment. To insure against this, the triplet codons corresponding to the desired polypeptide must be aligned in multiples of three from the initiation codon, i.e. the correct "reading frame" must be maintained. In the creation of fusion proteins containing a chelating peptide, the reading frame of the DNA sequence encoding the structural protein must be maintained in the DNA sequence encoding the chelating peptide.

Recombinant DNA Cloning Vector—any autonomously replicating agent including, but not limited to, plasmids and phages, comprising a DNA molecule to which one or more additional DNA segments can or have been added.

Recombinant DNA Expression Vector—any recombinant DNA cloning vector in which a promoter has been incorporated.

Recombinant Host Cell—Any cell transformed using a recombinant DNA Vector and which is capable of either replicating or transcribing and translating DNA used to construct the recombinant DNA Vector.

Replicon—A DNA sequence that controls and allows for autonomous replication of a plasmid or other vector.

Transcription—the process whereby information contained in a nucleotide sequence of DNA is transferred to a complementary RNA sequence.

Translation—the process whereby the genetic information of messenger RNA is used to specify and direct the synthesis of a polypeptide chain.

Treating—describes the management and care of a human or veterinary patient for the purpose of combating a disease, condition, or disorder, of the patient. Treating includes the administration of a compound of present invention to prevent the onset of the symptoms or complications, alleviating the symptoms or complications, eliminating the disease, condition, or disorder. Treating therefore includes the inhibition of food intake, the inhibition of weight gain, and inducing weight loss in patients in need thereof.

Vector—a replicon used for the transformation of cells in gene manipulation bearing polynucleotide sequences corresponding to appropriate protein molecules which, when combined with appropriate control sequences, confer specific properties on the host cell to be transformed. Plasmids, viruses, and bacteriophage are suitable vectors, since they are replicons in their own right. Artificial vectors are constructed by cutting and joining DNA molecules from different sources using restriction enzymes and ligases. Vectors include Recombinant DNA cloning vectors and Recombinant DNA expression vectors.

The amino acids abbreviations are accepted by the United States Patent and Trademark Office as set forth in 37 C.F.R. §1.822 (b) (2) (1993). Unless otherwise indicated the amino acids are in the L configuration.

In one embodiment, the invention provides nucleic acid molecules that encode a novel Rhesus ob gene product which is defined by the following amino acid sequence.

```
1               5                       10                  15   SEQ ID NO: 2
Val Pro Ile Gln Lys Val Gln Ser Asp Thr Lys Thr Leu Ile Lys 20                      25                  30
Thr Ile Val Thr Arg Ile Asn Asp Ile Ser His Thr Gln Ser Val 35                      40                  45
Ser Ser Lys Gln Arg Val Thr Gly Leu Asp Phe Ile Pro Gly Leu 50                      55                  60
His Pro Val Leu Thr Leu Ser Gln Met Asp Gln Thr Leu Ala Ile 65                      70                  75
Tyr Gln Gln Ile Leu Ile Asn Leu Pro Ser Arg Asn Val Ile Gln 80                      85                  90
Ile Ser Asn Asp Leu Glu Asn Leu Arg Asp Leu Leu His Leu Leu 95                      100                 105
Ala Phe Ser Lys Ser Cys His Leu Pro Leu Ala Ser Gly Leu Glu 110                     115                 120
Thr Leu Glu Ser Leu Gly Asp Val Leu Glu Ala Ser Leu Tyr Ser 125                     130                 135
Thr Glu Val Val Ala Leu Ser Arg Leu Gln Gly Ser Leu Gln Asp 140                     145
Met Leu Trp Gln Leu Asp Leu Ser Pro Gly Cys-COOH
```

A preferred coding region for the above embodiment is defined by the following DNA sequence.

```
5'- GTG CCC ATC CAA AAA GTC CAA AGT GAC ACC AAA ACC CTC ATC    SEQ ID NO: 1
    AAG ACA ATT GTC ACC AGG ATC AAT GAC ATT TCA CAC ACG CAG TCG
    GTC TCC TCC AAA CAG AGG GTC ACT GGT TTG GAC TTC ATT CCT GGG
    CTC CAC CCC GTC CTG ACC TTA TCC CAG ATG GAC CAG ACA CTG GCA
    ATC TAC CAA CAG ATC CTC ATC AAT CTG CCT TCC AGA AAC GTG ATC
    CAA ATA TCC AAC GAC TTG GAG AAT CTC CGG GAC CTT CTT CAC CTG
    CTG GCC TTC TCT AAG AGC TGC CAT TTG CCC TTG GCC AGT GGC CTG
```

-continued

GAG ACC TTG GAG AGC CTG GGG GAT GTC CTG GAA GCT TCA CTC TAC

TCC ACG GAG GTG GTG GCC CTG AGC AGG CTG CAG GGG TCT CTG CAG

GAC ATG CTG TGG CAG CTG GAC CTC AGC CCT GGG TGC -3'

The proteins of the present invention may be produced either by recombinant DNA technology or well known chemical procedures, such as solution or solid-phase peptide synthesis, or semi-synthesis in solution beginning with protein fragments coupled through conventional solution methods.

The principles of solid phase chemical synthesis of polypeptides are well known in the art and may be found in general texts in the area such as Dugas, H. and Penney, C., *Bioorganic Chemistry* Springer-Verlag, New York, pgs. 54–92 (1981). For example, peptides may be synthesized by solid-phase methodology utilizing an PE-Applied Biosystems 430A peptide synthesizer (commercially available from Applied Biosystems, Foster City Calif.) and synthesis cycles supplied by Applied Biosystems. Boc amino acids and other reagents are commercially available from PE-Applied Biosystems and other chemical supply houses. Sequential Boc chemistry using double couple protocols are applied to the starting p-methyl benzhydryl amine resins for the production of C-terminal carboxamides. For the production of C-terminal acids, the corresponding PAM resin is used. Arginine, Asparagine, Glutamine, Histidine and Methionine are coupled using performed hydroxy benzotriazole esters. The following side chain protection may be used:

Arg, Tosyl
Asp, cyclohexyl or benzyl
Cys, 4-methylbenzyl
Glu, cyclohexyl
His, benzyloxymethyl
Lys, 2-chlorobenzyloxycarbonyl
Met, sulfoxide
Ser, Benzyl
Thr, Benzyl
Trp, formyl
Tyr, 4-bromo carbobenzoxy Boc deprotection may be accomplished with trifluoroacetic acid (TFA) in methylene chloride. Formyl removal from Trp is accomplished by treatment of the peptidyl resin with 20% piperidine in dimethylformamide for 60 minutes at 4° C. Met(O) can be reduced by treatment of the peptidyl resin with TFA/dimethylsulfide/conHCl (95/5/1) at 25° C. for 60 minutes. Following the above pre-treatments, the peptides may be further deprotected and cleaved from the resin with anhydrous hydrogen fluoride containing a mixture of 10% m-cresol or m-cresol/10% p-thiocresol or m-cresol/p-thiocresol/dimethylsulfide. Cleavage of the side chain protecting group(s) and of the peptide from the resin is carried out at zero degrees Centigrade or below, preferably −20° C. for thirty minutes followed by thirty minutes at 0° C. After removal of the HF, the peptide/resin is washed with ether. The peptide is extracted with glacial acetic acid and lyophilized. Purification is accomplished by reverse-phase C18 chromatography (Vydac) column in 0.1% TFA with a gradient of increasing acetonitrile concentration. One skilled in the art recognizes that the solid phase synthesis could also be accomplished using the FMOC strategy and a TFA/scavenger cleavage mixture.

The claimed DNA sequences are useful for expressing the Rhesus ob gene product either by direct expression or as fusion protein. When the claimed sequences are used in a fusion gene, the resulting product will require enzymatic or chemical cleavage. A variety of peptidases which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See U.S. Pat. No. 5,126,249; Carter P., Site Specific Proteolysis of Fusion Proteins, Ch. 13 in *Protein Purification: From Molecular Mechanisms to Large Scale Processes,* American Chemical Soc., Washington, D.C. (1990).

Construction of suitable vectors containing the desired coding and control sequences employ standard ligation techniques. Isolated plasmids or DNA fragments are cleaved, tailored, and religated in the form desired to form the plasmids required.

To effect the translation of the desired protein, one inserts the engineered synthetic DNA sequence in any of a plethora of appropriate recombinant DNA expression vectors through the use of appropriate restriction endonucleases. The claimed protein is a relatively large protein. A synthetic coding sequence is designed to possess restriction endonuclease cleavage sites at either end of the transcript to facilitate isolation from and integration into these expression and amplification and expression plasmids. The isolated cDNA coding sequence may be readily modified by the use of synthetic linkers to facilitate the incorporation of this sequence into the desired cloning vectors by techniques well known in the art. The particular endonucleases employed will be dictated by the restriction endonuclease cleavage pattern of the parent expression vector to be employed. The restriction sites are chosen so as to properly orient the coding sequence with control sequences to achieve proper in-frame reading and expression of the claimed protein.

In general, plasmid vectors containing promoters and control sequences which are derived from species compatible with the host cell are used with these hosts. The vector ordinarily carries a replication origin as well as marker sequences which are capable of providing phenotypic selection in transformed cells. For example, *E. coli* is typically transformed using pBR322, a plasmid derived from an *E. coli* species (Bolivar, et al., *Gene* 2: 95 (1977)). Plasmid pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA technology.

The desired coding sequence is inserted into an expression vector in the proper orientation to be transcribed from a promoter and ribosome binding site, both of which should be functional in the host cell in which the protein is to be expressed. An example of such an expression vector is a plasmid described in Belagaje et al., U.S. Pat. No. 5,304,493, the teachings of which are herein incorporated by reference. The gene encoding A-C-B proinsulin described in U.S. Pat. No. 5,304,493 can be removed from the plasmid pRB182 with restriction enzymes NdeI and BamHI. The claimed DNA sequences of the present invention can be inserted into the plasmid backbone on a NdeI/BamHI restriction fragment cassette.

In general, procaryotes are used for cloning of DNA sequences in constructing the vectors useful in the invention. For example, E. coli K12 strain 294 (ATCC No. 31446) is particularly useful. Other microbial strains which may be used include E. coli B and E. coli X1776 (ATCC No. 31537). These examples are illustrative rather than limiting.

Procaryotes also are used for expression. The aforementioned strains, as well as E. coli W3110 (prototrophic, ATCC No. 27325), bacilli such as Bacillus subtilis, and other enterobacteriaceae such as Salmonella typhimurium or Serratia marcescans, and various pseudomonas species may be used. Promoters suitable for use with prokaryotic hosts include the b-lactamase (vector pGX2907 [ATCC 39344] contains the replicon and b-lactamase gene) and lactose promoter systems (Chang et al., Nature, 275:615 (1978); and Goeddel et al., Nature 281:544 (1979)), alkaline phosphatase, the tryptophan (trp) promoter system (vector pATH1 [ATCC 37695] is designed to facilitate expression of an open reading frame as a trpE fusion protein under control of the trp promoter) and hybrid promoters such as the tac promoter (isolatable from plasmid pDR540 ATCC-37282). However, other functional bacterial promoters, whose nucleotide sequences are generally known, enable one of skill in the art to ligate them to DNA encoding the protein using linkers or adaptors to supply any required restriction sites. Promoters for use in bacterial systems also will contain a Shine-Dalgarno sequence operably linked to the DNA encoding protein.

The claimed nucleic acid molecules may also be recombinantly produced in eukaryotic expression systems. Preferred promoters controlling transcription in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. b-actin promoter. The early and late promoters of the SV40 virus are conveniently obtained as an SV40 restriction fragment which also contains the SV40 viral origin of replication. Fiers, et al., Nature, 273:113 (1978). The entire SV40 genome may be obtained from plasmid pBRSV, ATCC 45019. The immediate early promoter of the human cytomegalovirus may be obtained from plasmid pCMBb (ATCC 77177). Of course, promoters from the host cell or related species also are useful herein.

Transcription of the claimed DNA by higher eucaryotes is increased by inserting an enhancer sequence into the vector. Enhancers are cis-acting elements of DNA, usually about 10–300 bp, that act on a promoter to increase its transcription. Enhancers are relatively oriented and positioned independently and have been found 5' (Laimins, L. et al., PNAS 78:993 (1981)) and 3' (Lusky, M. L., et al., Mol. Cell Bio. 3:1108 (1983)) to the transcription unit, within an intron (Banerji, J. L. et al., Cell 33:729 (1983)) as well as within the coding sequence itself (Osborne, T. F., et al., Mol. Cell Bio. 4:1293 (1984)). Many enhancer sequences are now known from mammalian genes (globin, RSV, SV40, EMC, elastase, albumin, a-fetoprotein and insulin). Typically, however, one will use an enhancer from a eukaryotic cell virus. Examples include the SV40 late enhancer, the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells from other multicellular organisms) will also contain sequences necessary for the termination of transcription which may affect mRNA expression. These regions are transcribed as polyadenylated segments in the untranslated portion of the mRNA encoding protein. The 3' untranslated regions also include transcription termination sites.

Expression vectors may contain a selection gene, also termed a selectable marker. Examples of suitable selectable markers for mammalian cells are dihydrofolate reductase (DHFR, which may be derived from the BglII/HindIII restriction fragment of pJOD-10 [ATCC 68815]), thymidine kinase (herpes simplex virus thymidine kinase is contained on the BamHI fragment of vP-5 clone [ATCC 2028]) or neomycin (G418) resistance genes (obtainable from pNN414 yeast artificial chromosome vector [ATCC 37682]). When such selectable markers are successfully transferred into a mammalian host cell, the transfected mammalian host cell can survive if placed under selective pressure. There are two widely used distinct categories of selective regimes. The first category is based on a cell's metabolism and the use of a mutant cell line which lacks the ability to grow without a supplemented media. Two examples are: CHO DHFR$^-$ cells (ATCC CRL-9096) and mouse LTK$^-$ cells (L-M(TK-) ATCC CCL-2.3). These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in nonsupplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, Southern P. and Berg, P., J. Molec. Aspl. Genet. 1: 327 (1982), mycophenolic acid, Mulligan, R. C. and Berg, P. Science 209:1422 (1980), or hygromycin, Sugden, B. et al., Mol Cell. Biol. 5:410—413 (1985). The three examples given above employ bacterial genes under eukaryotic control to convey resistance to the appropriate drug G418 or neomycin (geneticin), xgpt (mycophenolic acid) or hygromycin, respectively.

A preferred vector for eucaryotic expression is pRc/CMV. pRc/CMV is commercially available from Invitrogen Corporation, 3985 Sorrento Valley Blvd., San Diego, Calif. 92121. To confirm correct sequences in plasmids constructed, the ligation mixtures are used to transform E. coli K12 strain DH10B (ATCC 31446) and successful transformants selected by antibiotic resistance where appropriate. Plasmids from the transformants are prepared, analyzed by restriction and/or sequence by the method of Messing, et al., Nucleic Acids Res. 9:309 (1981).

Host cells may be transformed with the expression vectors of this invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan. The techniques of transforming cells with the aforementioned vectors are well known in the art and may be found in such general references as Maniatis, et al., Molecular Cloning: A Laboratory Manual, Cold Spring Harbor Press, Cold Spring Harbor Laboratory, Cold Spring Harbor, N.Y. (1989), or Current Protocols in Molecular Biology (1989) and supplements.

Preferred suitable host cells for expressing the vectors encoding the claimed proteins in higher eucaryotes include: African green monkey kidney line cell line transformed by SV40 (COS-7, ATCC CRL-1651); transformed human primary embryonal kidney cell line 293, (Graham, F. L. et al., J. Gen Virol. 36:59–72 (1977), Virology 77:319–329, Virology 86:10–21); baby hamster kidney cells (BHK-21(C-13), ATCC CCL-10, Virology 16:147 (1962)); chinese hamster ovary cells CHO-DHFR⁻ (ATCC CRL-9096), mouse Sertoli cells (TM4, ATCC CRL-1715, Biol. Reprod. 23:243–250 (1980)); african green monkey kidney cells (VERO 76, ATCC CRL-1587); human cervical epitheloid carcinoma cells (HeLa, ATCC CCL-2); canine kidney cells (MDCK, ATCC CCL-34); buffalo rat liver cells (BRL 3A, ATCC CRL-1442); human diploid lung cells (WI-38, ATCC CCL-75); human hepatocellular carcinoma cells (Hep G2, ATCC HB-8065); and mouse mammary tumor cells (MMT 060562, ATCC CCL51).

In addition to prokaryotes, unicellular eukaryotes such as yeast cultures may also be used. *Saccharomyces cerevisiae,* or common baker's yeast is the most commonly used eukaryotic microorganism, although a number of other strains are commonly available. For expression in Saccharomyces, the plasmid YRp7, for example, (ATCC-40053, Stinchcomb, et al., *Nature* 282:39 (1979); Kingsman et al., *Gene* 7:141 (1979); Tschemper et al., *Gene* 10:157 (1980)) is commonly used. This plasmid already contains the trp gene which provides a selection marker for a mutant strain of yeast lacking the ability to grow in tryptophan, for example ATCC no. 44076 or PEP4-1 (Jones, *Genetics* 85:12 (1977)).

Suitable promoting sequences for use with yeast hosts include the promoters for 3-phosphoglycerate kinase (found on plasmid pAP12BD ATCC 53231 and described in U.S. Pat. No. 4,935,350, Jun. 19, 1990) or other glycolytic enzymes such as enolase (found on plasmid pAC1 ATCC 39532), glyceraldehyde-3-phosphate dehydrogenase (derived from plasmid pHcGAPC1 ATCC 57090, 57091), zymomonas mobilis (U.S. Pat. No. 5,000,000 issued Mar. 19, 1991), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which contain inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein (contained on plasmid vector pCL28XhoLHBPV ATCC 39475, U.S. Pat. No. 4,840,896), glyceraldehyde 3-phosphate dehydrogenase, and enzymes responsible for maltose and galactose (GAL1 found on plasmid pRY121 ATCC 37658) utilization. Suitable vectors and promoters for use in yeast expression are further described in R. Hitzeman et al., European Patent Publication No. 73,657A. Yeast enhancers such as the UAS Gal from *Saccharomyces cerevisiae* (found in conjunction with the CYC1 promoter on plasmid YEpsec—hI1beta ATCC 67024), also are advantageously used with yeast promoters.

The following examples will help describe how the invention is practiced and will illustrate the characteristics of the claimed DNA molecules, vectors, host cells, and methods of the invention.

EXAMPLE 1

PCR Amplification

Degenerate primers were designed based on the published DNA sequence of region flanking the human ob gene. The primers were prepared for use in polymerase chain reaction (PCR) amplification methods using a Model 380A DNA synthesizers (PE-Applied Biosystems, Inc., 850 Lincoln Center Drive, Foster City, Calif. 94404). Forward primer: 5'-CCC AAG AAG CCC ATC CTG GGA AGG AAA ATG-3' (SEQ ID NO: 3) and reverse primer: 5'-CTT GCA GGA AGA GTG ACC TTC AAG GCC TCA-3' (SEQ ID NO: 4) were mixed together with PCR-ready Rhesus fat cell cDNA as the template prepared in the following manner.

Rhesus monkey adipose tissue was obtained from two individuals (designated 2810 and 2820) which are a part of a colony of Rhesus monkeys housed in Eli Lilly and Company's toxicology labs in Greenfield, Ind. Both samples of adipose tissue were handled identically and worked on in parallel. Total RNA was isolated using guanidine thiocyanate and ultracentrifugation method. The cDNA was synthesized using 5 ug of total RNA and the SuperScript preamplification system commercially available from GIBCO-BRL (Grand Island, N.Y.). Reverse transcription was primed with oligo dT primers provided in the kit.

PCR amplification was performed by mixing 2 uL of cDNA generated in the reverse transcription step with approximately 20 pmoles of forward and reverse primers, and 2 units of Vent DNA polymerase® (New England Biolabs). The amplification was carried out in 35 amplification cycles (94° C.–30 sec, 57° C.–30 sec, 72° C.–45 sec) preceded by HotStart at 80° C.

The PCR product was gel purified and cloned into a pCR-SCRIPT® cloning vector (Stratagene). The vector was then used to transform *E. coli* cells. Plasmid DNA was isolated from several white colonies and sequenced using standard DNA sequencing methods.

EXAMPLE 2

Vector Construction

A plasmid containing the DNA sequence encoding the desired claimed protein is constructed to include NdeI and BamHI restriction sites. The plasmid carrying the cloned PCR product is digested with MunI and BamHI restriction enzymes. The small ~400 bp fragment is gel-purified. The synthetic oligonucletide linker is used to reconstruct the front part of the DNA up to MunI site and to introduce NdeI restriction sight and codons for Met-Arg. The synthetic linker, the 400 bp fragment, and pBR182 vector whose A-C-B proinsulin coding region is absent are ligated in a three piece ligation.

The ligation products are transformed into *E. coli* DH10B (commercially available from GIBCO-BRL) and colonies growing on tryptone-yeast (DIFCO) plates supplemented with 10 mg/mL of tetracycline are analyzed. Plasmid DNA is isolated, digested with NdeI and BamHI and the resulting fragments are separated by agarose gel electrophoresis. Plasmids containing the expected ~400 bp NdeI to BamHI fragment are kept. *E. coli* K12 RV308 (available from the NRRL under deposit number B-15624) are transformed with this second plasmid, resulting in a culture suitable for expressing the protein.

The techniques of transforming cells with the aforementioned vectors are well known in the art and may be found in such general references as Maniatis, et al. (1988) *Molecular Cloning: A Laboratory Manual,* Cold Spring Harbor Press, Cold Spring Harbor Laboratory, Cold Spring Harbor, N.Y. or *Current Protocols in Molecular Biology* (1989) and supplements. The techniques involved in the transformation of *E. coli* cells used in the preferred practice of the invention as exemplified herein are well known in the art. The precise conditions under which the transformed *E. coli* cells are cultured is dependent on the nature of the *E. coli* host cell line and the expression or cloning vectors employed. For example, vectors which incorporate thermoinducible promoter-operator regions, such as the c1857 thermoinducible lambda-phage promoter-operator region, require a temperature shift from about 30 to about 40 degrees C. in the culture conditions so as to induce protein synthesis.

In the preferred embodiment of the invention, *E. coli* K12 RV308 cells are employed as host cells but numerous other cell lines are available such as, but not limited to, *E. coli* K12 L201, L687, L693, L507, L640, L641, L695, L814 (*E. coli* B). The transformed host cells are then plated on appropriate media under the selective pressure of the antibiotic corresponding to the resistance gene present on the expression plasmid. The cultures are then incubated for a time and temperature appropriate to the host cell line employed.

Proteins which are expressed in high-level bacterial expression systems characteristically aggregate in granules or inclusion bodies which contain high levels of the overexpressed protein. Kreuger et al., in *Protein Folding*, Gierasch and King, eds., pgs 136–142 (1990), American Association for the Advancement of Science Publication No. 89-18S, Washington, D.C. Such protein aggregates must be solubilized to provide further purification and isolation of the desired protein product. Id. A variety of techniques using strongly denaturing solutions such as guanidinium-HCl and/ or weakly denaturing solutions such as dithiothreitol (DTT) are used to solubilize the proteins. Gradual removal of the denaturing agents (often by dialysis) in a solution allows the denatured protein to assume its native conformation. The particular conditions for denaturation and folding are determined by the particular protein expression system and/or the protein in question.

Preferably, the present DNA sequences are expressed with a dipeptide leader sequence encoding Met-Arg or Met-Tyr as described in U.S. Pat. No. 5,126,249, herein incorporated by reference. This approach facilitates the efficient expression of proteins and enables rapid conversion to the active protein form with Cathepsin C or other dipeptidylpeptidases. The purification of proteins is by techniques known in the art and includes reverse phase chromatography, affinity chromatography, and size exclusion.

EXAMPLE 3

Biological Testing

Parabiotic experiments suggest that a protein is released by peripheral adipose tissue and that the protein is able to control body weight gain in normal, as well as obese mice. Therefore, the most closely related biological test is to inject the test article by any of several routes of administration (i.v., s.c., i.m., i.p., or by minipump or cannula) and then to monitor food and water consumption, body weight gain, plasma chemistry or hormones (glucose, insulin, ACTH, corticosterone, GH, T4) over various time periods.

Suitable test animals include normal mice (ICR, etc.) and obese mice (ob/ob, Avy/a, KK-Ay, tubby, fat). The ob/ob mouse model of obesity and diabetes is generally accepted in the art as being indicative of the obesity condition. Controls for non-specific effects for these injections are done using vehicle with or without the active agent of similar composition in the same animal monitoring the same parameters or the active agent itself in animals that are thought to lack the receptor (db/db mice, fa/fa or cp/cp rats). Proteins demonstrating activity in these models will demonstrate similar activity in other mammals, particularly humans.

Since the target tissue is expected to be the hypothalamus where food intake and lipogenic state are regulated, a similar model is to inject the test article directly into the brain (e.g. i.c.v. injection via lateral or third ventricles, or directly into specific hypothalamic nuclei (e.g. arcuate, paraventricular, perifornical nuclei). The same parameters as above could be measured, or the release of neurotransmitters that are known to regulate feeding or metabolism could be monitored (e.g. NPY, galanin, norepinephrine, dopamine, b-endorphin release).

Similar studies are accomplished in vitro using isolated hypothalamic tissue in a perifusion or tissue bath system. In this situation, the release of neurotransmitters or electrophysiological changes is monitored.

Proteins expressed by the claimed DNA sequences are believed to be active in at least one of the above biological tests and are anti-obesity agents. As such, the claimed DNA sequences are useful for preparing protein compositions for treating obesity and disorders implicated by obesity. However, the claimed DNA sequences are also useful for preparing immunogens to raise antibodies for diagnostic use.

---

We claim:

1. An isolated nucleic acid molecule consisting of a nucleotide sequence that encodes a protein having the following amino acid sequence:

(SEQ ID NO: 2)

NH$_2$-Val Pro Ile Gln Lys Val Gln Ser Asp Thr Lys

Thr Leu Ile Lys Thr Ile Val Thr Arg Ile Asn Asp

Ile Ser His Thr Gln Ser Val Ser Ser Lys Gln Arg

Val Thr Gly Leu Asp Phe Ile Pro Gly Leu His Pro

Val Leu Thr Leu Ser Gln Met Asp Gln Thr Leu Ala

Ile Tyr Gln Gln Ile Leu Ile Asn Leu Pro Ser Arg

Asn Val Ile Gln Ile Ser Asn Asp Leu Glu Asn Leu

Arg Asp Leu Leu His Leu Leu Ala Phe Ser Lys Ser

Cys His Leu Pro Leu Ala Ser Gly Leu Glu Thr Leu

Glu Ser Leu Gly Asp Val Leu Glu Ala Ser Leu Tyr

Ser Thr Glu Val Val Ala Leu Ser Arg Leu Gln Gly

Ser Leu Gln Asp Met Leu Trp Gln Leu Asp Leu Ser

Pro Gly Cys-COOH.

2. A nucleic acid molecule of claim 1 consisting of DNA having the following nucleotide sequence:

```
5'- GTG CCC ATC CAA AAA GTC CAA AGT GAC ACC AAA ACC CTC ATC    (SEQ ID NO: 1)

AAG ACA ATT GTC ACC AGG ATC AAT GAC ATT TCA CAC ACG CAG TCG

GTC TCC TCC AAA CAG AGG GTC ACT GGT TTG GAC TTC ATT CCT GGG

CTC CAC CCC GTC CTG ACC TTA TCC CAG ATG GAC CAG ACA CTG GCA

ATC TAC CAA CAG ATC CTC ATC AAT CTG CCT TCC AGA AAC GTG ATC

CAA ATA TCC AAC GAC TTG GAG AAT CTC CGG GAC CTT CTT CAC CTG

CTG GCC TTC TCT AAG AGC TGC CAT TTG CCC TTG GCC AGT GGC CTG

GAG ACC TTG GAG AGC CTG GGG GAT GTC CTG GAA GCT TCA CTC TAC

TCC ACG GAG GTG GTG GCC CTG AGC AGG CTG CAG GGG TCT CTG CAG

GAC ATG CTG TGG CAG CTG GAC CTC AGC CCT GGG TGC -3'.
```

3. A recombinant DNA vector comprising a nucleic acid molecule of claim 1.

4. A recombinant DNA vector comprising the DNA molecule of claim 2.

5. A recombinant host cell comprising a vector of claim 3.

6. A recombinant host cell comprising a vector of claim 4.

7. A method for producing an anti-obesity protein comprising:

a) culturing a host cell of claim 5; and,
   b) isolating a protein comprising an amino acid sequence of SEQ ID NO: 2.

8. A method for producing an anti-obesity protein comprising:

a) culturing a host cell of claim 6; and,
   b) isolating a protein comprising an amino acid sequence of SEQ ID NO: 2.

\* \* \* \* \*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:1:

```
Val Pro Ile Gln Lys Val Gln Ser Asp Thr Lys Thr Leu Ile Lys Thr
 1               5                  10                  15

Ile Val Thr Arg Ile Asn Pro Ile Ser His Thr Gln Ser Val Ser Ser
                20                  25                  30
```

―continued

```
Lys Gln Arg Val Thr Gly Leu Pro Phe Ile Pro Gly Leu His Pro Val
     35                  40                  45

Leu Thr Leu Ser Gln Met Pro Gln Thr Leu Ala Ile Tyr Gln Gln Ile
     50                  55                  60

Leu Ile Asn Leu Pro Ser Arg Asn Val Ile Gln Ile Ser Asn Asp Leu
65                   70                  75                  80

Glu Asn Leu Arg Asp Leu Leu His Leu Leu Ala Phe Ser Lys Ser Cys
             85                  90                  95

His Leu Pro Leu Ala Ser Gly Leu Glu Thr Leu Glu Ser Leu Gly Asp
            100                 105                 110

Val Leu Glu Ala Ser Leu Tyr Ser Thr Glu Val Val Ala Leu Ser Arg
            115                 120                 125

Leu Gln Gly Ser Leu Gln Ala Met Leu Trp Gln Leu Asp Leu Ser Pro
    130                 135                 140

Gly Cys
145

(2) INFORMATION FOR SEQ ID NO:2:

(i) SEQUENCE CHARACTERISTICS:
        (A) LENGTH: 438 base pairs
        (B) TYPE: nucleic acid
        (C) STRANDEDNESS: single
        (D) TOPOLOGY: linear (ii) MOLECULE TYPE: protein (xi) SEQUENCE DESCRIPTION: SEQ ID NO:2:

GTGCCCATCC AAAAAGTCCA AAGTGACACC AAAACCCTCA TCAAGACAAT TGTCACCAGG      60

ATCAATGACA TTTCACACAC GCAGTCGGTC TCCTCCAAAC AGAGGGTCAC TGGTTTGGAC     120

TTCATTCCTG GGCTCCACCC CGTCCTGACC TTATCCCAGA TGGACCAGAC ACTGGCAATC     180

TACCAACAGA TCCTCATCAA TCTGCCTTCC AGAAACGTGA TCCAAATATC CAACGACTTG     240

GAGAATCTCC GGGACCTTCT TCACCTGCTG GCCTTCTCTA AGAGCTGCCA TTTGCCCTTG     300

GCCAGTGGCC TGGAGACCTT GGAGAGCCTG GGGGATGTCC TGGAAGCTTC ACTCTACTCC     360

ACGGAGGTGG TGGCCCTGAG CAGGCTGCAG GGGTCTCTGC AGGACATGCT GTGGCAGCTG     420

GACCTCAGCC CTGGGTGC                                                   438
```